United States Patent
Tanzer

(10) Patent No.: US 10,842,673 B2
(45) Date of Patent: Nov. 24, 2020

(54) RETINAL IMAGING FOR REFERENCE DURING LASER EYE SURGERY

(71) Applicant: AMO Development, LLC, Santa Ana, CA (US)

(72) Inventor: David J. Tanzer, San Diego, CA (US)

(73) Assignee: AMO Development, LLC, Santa Ana, CA (US)

( * ) Notice: Subject to any disclaimer, the term of this patent is extended or adjusted under 35 U.S.C. 154(b) by 406 days.

(21) Appl. No.: 15/643,257

(22) Filed: Jul. 6, 2017

(65) Prior Publication Data

US 2018/0008460 A1 Jan. 11, 2018

Related U.S. Application Data

(60) Provisional application No. 62/359,014, filed on Jul. 6, 2016.

(51) Int. Cl.
*A61F 9/008* (2006.01)
*A61B 3/00* (2006.01)
(Continued)

(52) U.S. Cl.
CPC ............ *A61F 9/008* (2013.01); *A61B 3/0025* (2013.01); *A61B 3/0083* (2013.01); *A61B 3/102* (2013.01);
(Continued)

(58) Field of Classification Search
CPC .... A61F 9/008; A61F 2/1662; A61F 9/00804; A61F 9/00812; A61F 2009/00851;
(Continued)

(56) References Cited

U.S. PATENT DOCUMENTS 5,002,384 A 3/1991 Trachtman
6,120,461 A 9/2000 Smyth
(Continued)

FOREIGN PATENT DOCUMENTS

CA 2353921 A1 6/2000
CN 103458771 A 12/2013
(Continued)

OTHER PUBLICATIONS

International Search Report and Written Opinion for Application No. PCT/US2017/040957, dated Oct. 12, 2017, 12 pages.
(Continued)

*Primary Examiner* — Michael W Kahelin
*Assistant Examiner* — Shirley X Jian
(74) *Attorney, Agent, or Firm* — Johnson & Johnson Surgical Vision, Inc.

(57) ABSTRACT

A method of laser eye surgery including linking retinal vessel architecture to corneal topography. This enables registration of the steep axis of the cornea in order to orient a toric intraocular lens, and/or to place astigmatic keratotomy incisions. First, a detailed pre-operative retinal image of the vasculature of the retina is obtained. In addition, a pre-operative image of the topography of the eye is obtained. The retinal image is then correlated or superimposed on the topography image to provide a reference. After the patient lies down under the laser eye surgery system, and during the surgery, the retinal vasculature is monitored which provides a reference to the surgery system about the topography of the eye. This process enables registration of the steep axis of the cornea in order to orient a toric intraocular lens and/or to place astigmatic keratotomy incisions.

16 Claims, 2 Drawing Sheets

(51) Int. Cl.
*A61B 3/10* (2006.01)
*A61B 3/107* (2006.01)
*A61B 3/12* (2006.01)
*A61B 3/14* (2006.01)
*A61F 2/16* (2006.01)
*A61G 15/02* (2006.01)

(52) U.S. Cl.
CPC ............... *A61B 3/107* (2013.01); *A61B 3/12* (2013.01); *A61B 3/14* (2013.01); *A61F 2/1662* (2013.01); *A61F 9/00804* (2013.01); *A61F 9/00812* (2013.01); *A61G 15/02* (2013.01); *A61F 2009/00851* (2013.01); *A61F 2009/00853* (2013.01); *A61F 2009/00872* (2013.01); *A61F 2009/00882* (2013.01)

(58) Field of Classification Search
CPC .. A61F 2009/00853; A61F 2009/00872; A61F 2009/00882; A61B 3/0025; A61B 3/102; A61B 3/107; A61B 3/12; A61B 3/14; A61G 15/02
USPC ....................................................... 606/4–10
See application file for complete search history.

(56) References Cited

U.S. PATENT DOCUMENTS

| | | | |
|---|---|---|---|
| 6,779,891 B1 | 8/2004 | Barth et al. | |
| 6,939,342 B2* | 9/2005 | Markman | A61B 3/1005 128/898 |
| 6,942,656 B2 | 9/2005 | Pawlowski et al. | |
| 7,044,602 B2* | 5/2006 | Chernyak | A61B 3/1015 351/208 |
| 7,431,457 B2* | 10/2008 | Chernyak | A61B 3/1015 351/208 |
| 7,480,396 B2* | 1/2009 | Teiwes | A61B 3/113 351/206 |
| 7,878,655 B2 | 2/2011 | Salvati et al. | |
| 8,128,228 B2 | 3/2012 | Van | |
| 8,137,399 B2 | 3/2012 | Glazier et al. | |
| 8,403,483 B2 | 3/2013 | Klink et al. | |
| RE44,226 E | 5/2013 | Nanjo | |
| 8,459,794 B2 | 6/2013 | Juhasz et al. | |
| 8,485,663 B2* | 7/2013 | Endo | A61B 3/112 351/212 |
| 8,491,122 B2 | 7/2013 | Hacker et al. | |
| 8,529,060 B2* | 9/2013 | Levis | A61F 2/16 351/204 |
| 8,540,370 B2 | 9/2013 | Norrby | |
| 8,596,790 B2 | 12/2013 | Salvati et al. | |
| 9,498,122 B2* | 11/2016 | Friedman | A61B 3/107 |
| 10,130,511 B2* | 11/2018 | Dantus | H01S 3/005 |
| 10,398,300 B2* | 9/2019 | Levis | A61B 3/0041 |
| 2002/0151877 A1 | 10/2002 | Mason | |
| 2004/0002694 A1 | 1/2004 | Pawlowski et al. | |
| 2005/0024586 A1* | 2/2005 | Teiwes | A61B 3/113 351/209 |
| 2008/0144771 A1* | 6/2008 | Gertner | A61N 5/1017 378/65 |
| 2008/0273173 A1* | 11/2008 | Grotehusmann | A61B 5/1171 351/206 |
| 2010/0152847 A1* | 6/2010 | Padrick | A61B 3/13 623/6.11 |
| 2010/0208199 A1 | 8/2010 | Levis et al. | |
| 2011/0149239 A1 | 6/2011 | Neal et al. | |
| 2011/0299034 A1* | 12/2011 | Walsh | A61B 3/102 351/206 |
| 2013/0070203 A1 | 3/2013 | Michaels et al. | |
| 2014/0058367 A1* | 2/2014 | Dantus | H01S 3/005 606/6 |
| 2014/0132922 A1 | 5/2014 | Padrick et al. | |

FOREIGN PATENT DOCUMENTS

| | | |
|---|---|---|
| GB | 2487873 A | 8/2012 |
| JP | 4373555 B2 | 11/2009 |
| JP | 1886389 B2 | 2/2012 |
| JP | 5052897 B2 | 10/2012 |
| JP | 2013094406 A | 5/2013 |
| JP | 5319009 B2 | 10/2013 |
| KR | 101410884 B1 | 6/2014 |
| WO | 0189373 A2 | 11/2001 |
| WO | 2011035063 A1 | 3/2011 |
| WO | 2012154278 A1 | 11/2012 |
| WO | 2012154597 A1 | 11/2012 |
| WO | 2015113917 A1 | 8/2015 |

OTHER PUBLICATIONS

Broehan A.M., et al., "Real-time Multimodal Retinal Image Registration for a Computer-Assisted Laser Photocoagulation System," IEEE Xplore: IEEE Transactions on Biomedical Engineering, Oct. 2011, vol. 58(10), pp. 2816-2824.

Lethaus B., et al., "Looking for Landmarks in Medial Orbital Trauma Surgery," International Journal of Oral and Maxillofacial Surgery, Feb. 2013, vol. 42 (2), pp. 209-213.

Shen H., et al., "Frame-Rate Spatial Referencing Based on Invariant Indexing and Alignment with Application to Online Retinal Image Registration," IEEE Transactions on Pattern Analysis and Machine Intelligence, Mar. 2003, vol. 25 (3), pp. 379-384.

Sunness J.S., et al., "Landmark-Driven Fundus Perimetry Using the Scanning Laser Ophthalmoscope," Investigative Ophthalmology & Visual Science, Aug. 1995, vol. 36 (9), pp. 1863-1874.

Zheng Y., et al., "Landmark Matching Based Retinal Image Alignment by Enforcing Sparsity in Correspondence Matrix," Medical Image Analysis, Aug. 2014, vol. 18 (6), pp. 903-913.

* cited by examiner

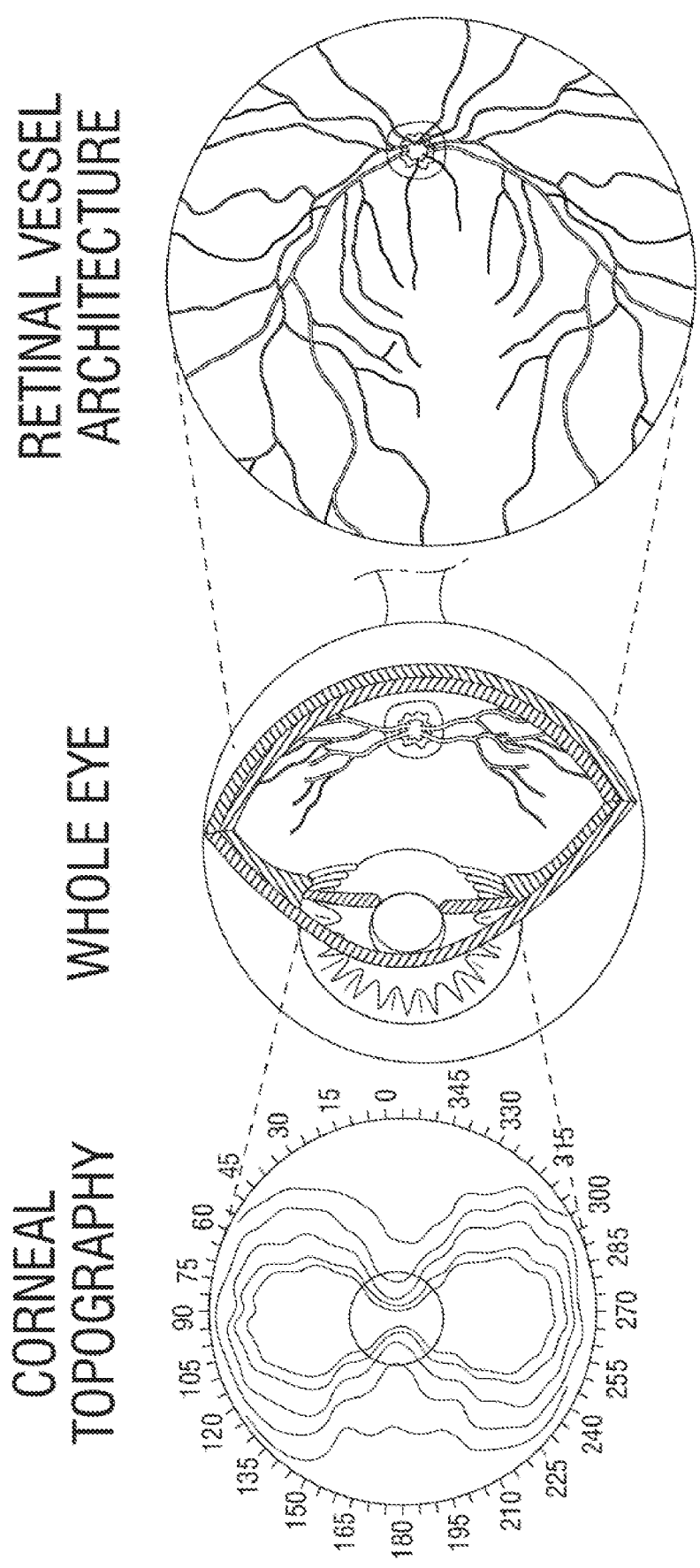

RETINAL IMAGING FOR REFERENCE DURING LASER EYE SURGERY

RELATED APPLICATIONS

This application claims priority to, and the benefit of, under 35 U.S.C. § 119(e) of U.S. Provisional Appl. No. 62/359,014, filed Jul. 6, 2016, which is incorporated herein by reference in its entirety.

FIELD OF THE INVENTION

The present application pertains to laser-assisted eye surgery and, more particularly, to methods of orienting a laser optical system to an astigmatic eye by pre-operative retinal imaging.

BACKGROUND

A cataract is formed by opacification of the crystalline lens or its envelope—the lens capsule—of the eye. The cataract obstructs passage of light through the lens. A cataract can vary in degree from slight to complete opacity. Early in the development of an age-related cataract, the power of the lens may be increased, causing near-sightedness (myopia). Gradual yellowing and opacification of the lens may reduce the perception of blue colors as those wavelengths are absorbed and scattered within the crystalline lens. Cataract formation typically progresses slowly resulting in progressive vision loss. If left untreated, cataracts may cause blindness.

Several commercial laser-assisted eye surgery systems are available to facilitate cataract removal and astigmatism correction. The CATALYS Precision Laser System from Abbott Medical Optics is indicated for anterior capsulotomy, phacofragmentation, and the creation of single plane and multi-plane arc cuts/incisions in the cornea to correct astigmatism. The CATALYS System uses a two-piece liquid-filled interface that docks with the patient's eye and provides a clear optical path for real-time video, OCT imaging, and laser treatment. Other systems for laser cataract surgery are the LenSx Laser from Alcon Laboratories, Inc., the LENSAR Laser System from LENSAR, Inc., and the VICTUS Femtosecond Laser Platform from TECHNOLAS Perfect Vision GmbH, a Bausch+Lomb Company.

Another laser procedure is laser-assisted in situ keratomileusis ("LASIK"), which is a refractive surgery that treats the cornea of the eye to correct myopia, hyperopia, and/or astigmatism. Since this procedure involves treatment within corneal tissue. it requires a "flap" to be created and lifted to expose a middle section of the cornea (the "stroma") for photoablation with an excimer laser. Previously, surgical tools such as microkeratomes were used to create corneal flaps. But, these clays, flaps are created and prepared using a non-ultraviolet, ultra-short pulsed laser that emits radiation in ultra-short pulse durations measured in as few as a few femtoseconds or a few nanoseconds. Examples of ultra-short pulsed laser systems include the Abbott Medical Optics iFS Advanced Femtosecond Laser, the Intralase FS Laser, as well as various other femtosecond and picosecond lasers available in the market.

One challenge during laser eye surgery is maintaining a precise understanding of the geography of the astigmatic patient's eye, especially between the stages where the patient is upright and supine on the treatment table. Presently, there are a number of ways for measuring the eye for proper alignment of toric intraocular lenses, incisional correction of astigmatism and laser application to the cornea. Typically, surgeons place marks on the eye using a surgical marking pen to serve as a reference point for alignment of toric intraocular lenses and other therapeutic applications such as making corneal incisions. Other imaging modalities exist for keeping track of the astigmatic eye during the surgery, including topography, ocular coherence tomography (OCT), wavefront sensing (including Marie Talbot interferometry used in WaveTec ORA), and video photography. None of these techniques is 100% accurate, and the need for continuous real-time monitoring of the position of the eye interferes with an efficient procedure.

Accordingly, there is a need for a simpler and more accurate way to convey the orientation and position of the eye to the laser surgery system.

SUMMARY

The present disclosure solves a number of deficiencies in prior techniques for monitoring the orientation and position of the eye during laser eye surgery. The method involves obtaining a pre-operative image of the terrain of the retina to which is then calibrated with an understanding of the topography of the eye. Subsequently, the registration between the retinal image and topography enables the laser to adapt to changing positions and orientations of the patient's eye during the surgery.

The methods disclosed herein involve linking retinal vessel architecture to corneal topography. This enables registration of the steep axis of the cornea in order to orient a toric intraocular lens and/or to place astigmatic keratotomy incisions.

The methods include use of retinal landmarks as reference marks for ocular alignment. The retinal landmarks would be determined from retinal images obtained preoperatively (before the surgery) and intraoperative (during surgery). Computer analysis would be conducted on the images to determine a misalignment measurement that a surgeon would use as a guide in placing the therapeutic product (e.g. IOL).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2 is a schematic diagram of methods disclosed herein for linking retinal vessel architecture with corneal topography.

DETAILED DESCRIPTION

Figure 1:
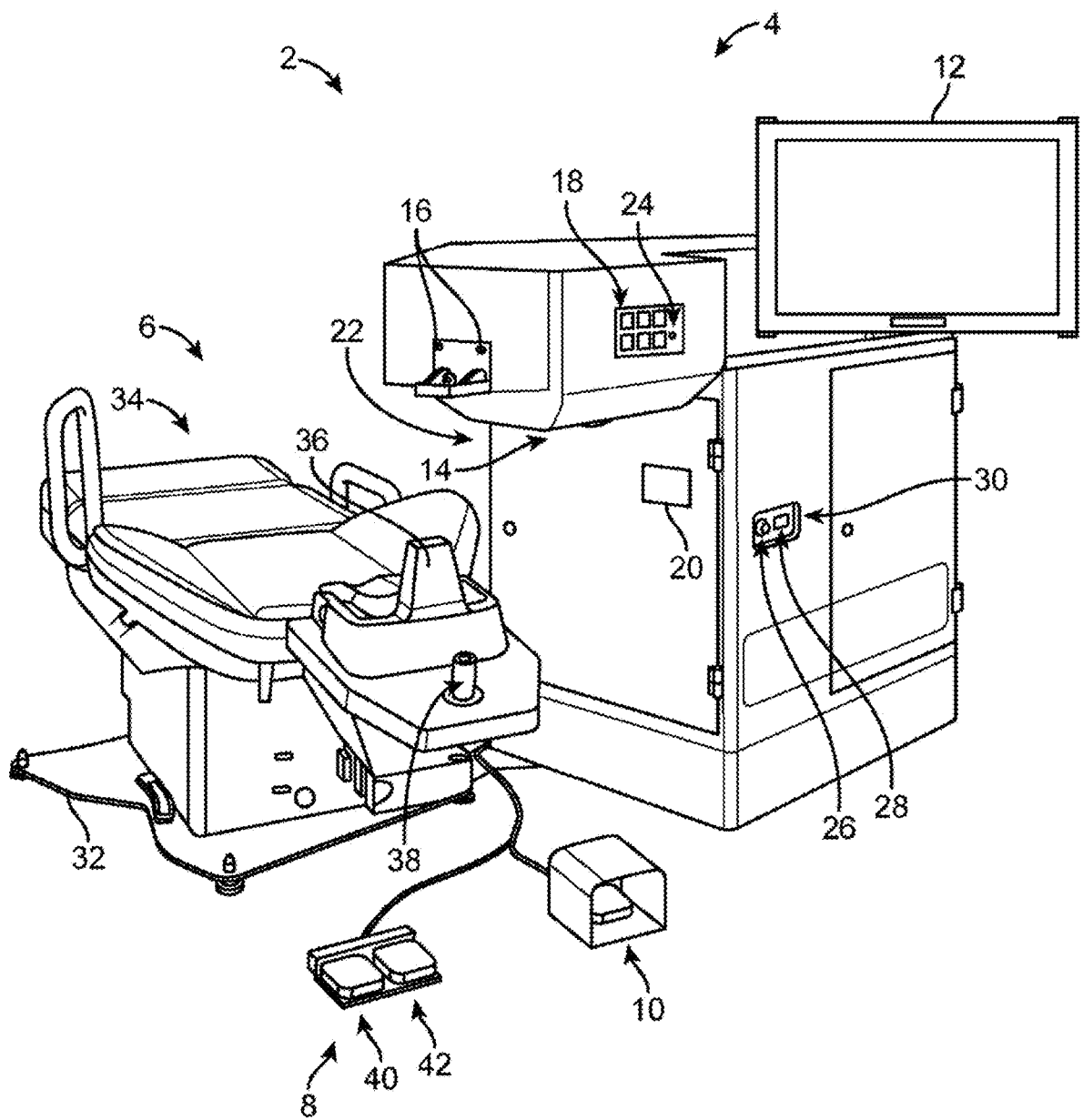
FIG. 1 is a perspective view showing an exemplary laser eye surgery system.

FIG. 1 shows an exemplary laser eye surgery system 2 operable to form precise incisions in the cornea, in the lens capsule, and/or in the crystalline lens nucleus. The methods described herein can be performed in conjunction with use of the laser eye surgery system 2 for a better and more accurate understanding of the location of the steep axis of the cornea in order to orient a toric intraocular lens and/or to place astigmatic keratotomy incisions.

The system 2 includes a diagnostic and interventional unit 4, a patient chair 6, a dual function footswitch 8, and a laser footswitch 10. The diagnostic and interventional unit 4 houses many primary subsystems of the system 2. For example, externally visible subsystems include a touchscreen control panel 12, a patient interface assembly 14, patient interface vacuum connections 16, a docking control keypad 18, a patient interface radio frequency identification (RFID) reader 20, external connections 22 (e.g., network, video output, footswitch, USB port, door interlock, and AC power), laser emission indicator 24, emergency laser stop button 26, key switch 28, and USB data ports 30. The emergency stop button 26 can be pushed to stop emission of all laser output, release vacuum that couples the patient to the system 2, and disable the patient chair 6. The stop button 26 is located on the system front panel, next to the key switch 28. Although not shown, a processor and memory are associated with the system 2 to provide precise control over a laser beam that passes through the patient interface assembly 14 to operate on a patient's eye.

The patient chair 6 includes a base 32, a patient support bed 34, a headrest 36, a positioning mechanism (internal, not shown), and a patient chair joystick control 38 disposed on the headrest 36. The positioning control mechanism is coupled between the base 32 and the patient support bed 34 and headrest 36. The patient chair 6 is configured to be adjusted and oriented in three axes (x, y, and z) using the patient chair joystick control 38. The headrest 36 and a restrain system (not shown, e.g., a restraint strap engaging the patient's forehead) stabilize the patient's head during the procedure. The headrest 36 includes an adjustable neck support to provide patient comfort and to reduce patient head movement. The headrest 36 is configured to be vertically adjustable to enable adjustment of the patient head position to provide patient comfort and to accommodate variation in patient head size.

The dual function footswitch 8 is a dual footswitch assembly that includes the left foot switch 40 and a right foot switch 42. The left foot switch 40 is the "chair enable" footswitch. The right footswitch 42 is a "vacuum ON" footswitch that enables vacuum to secure a liquid optics interface suction ring to the patient's eye. The laser footswitch 10 is a shrouded footswitch that activates the treatment laser when depressed while the system is enabled.

The patient chair 6 is equipped with a "chair enable" feature to protect against unintended chair motion. The patient chair joystick 38 can be enabled in either of two ways. First, the patient chair joystick 38 incorporates a "chair enable" button located on the top of the joystick. Control of the position of the patient chair 6 via the joystick 38 can be enabled by continuously pressing the "chair enable" button. Alternately, the left foot switch 40 of the dual function footswitch 8 can be continuously depressed to enable positional control of the patient chair 6 via the joystick 38.

One of the challenges is that when the patient goes from the upright preoperative environment to being supine on the surface of patient chair 6 during the procedure, some re-orientation of the eye is common relative to the position/orientation of the cranium, for example, and the surgeon must find a way to re-establish his understanding of the orientation of the eye anatomy relative to the interventional tools. Conventionally, the physician will conduct a preoperative examination with the patient in an upright position, and will make a series of marks with a pen upon the cornea and/or sclera to provide a temporary reference with regard to the astigmatic axis of the subject eye; this axis may be subsequently utilized during surgery when the patient reclines to place relaxing cuts, radial cuts, or other types of incisions, to tailor the geometry of capsular cuts, etc. Alternatively, a series of fiducial features and/or markers placed within the field of view of the imaging system to view the eye anatomy may be used to establish the eye orientation. These techniques have proved successful, but are not 100% accurate.

The present application contemplates a different methodology for preoperative examination which is then used to keep track of the steep axis of an astigmatic eye during the surgery, or other abnormalities. The method comprises imaging the retina as well as measuring the topography of the eye and combining the information so that knowledge of one will provide knowledge of the other. The method uses known, static retinal landmarks as reference marks for ocular alignment.

FIG. 2 schematically illustrates the calibration scheme. The physician or technician obtains an image of the retinal vessel architecture or optic nerve, as seen on the right, preferably using a high-resolution video camera. The retina features an intricate and static vasculature which provides a detailed reference map. The retinal images obtained during the pre-operative workup are registered in the system memory. At the same time (simultaneously or immediately thereafter) that the retinal image is obtained, a scan of the corneal topography is made such as with ocular coherence tomography (OCT). The two images are then correlated so that an understanding of the retinal image provides a reference for the corneal topography, and vice versa. Normally these pre-operative measurements are made with the patient sitting up, or at least not lying down under the laser surgery system.

After preparing the patient, he or she is positioned supine under the laser surgery system. Prior to conducting any procedure, the retina is imaged again, preferably with a high-resolution video camera. The second retinal image obtained intraoperatively enables the system to analyze the retinal vasculature and/or optic nerve to gauge misalignment of the eye (or head) compared to the pre-operative measurement. The system then alerts the surgeon of the misalignment and recommends rotation of the eye (head) in a specific direction (clockwise or counter-clockwise) and by a specific amount (in degrees or radians) to properly align the eye with the pre-operative measurements. Because the orientation of the eye is known and the orientation of a therapeutic modality is known (i.e., toric intraocular lens or arcuate keratotomies), a guide in the system can then provide feedback to the surgeon as to where to align the therapeutic modality.

In laser surgeries, the information obtained regarding the retinal images obtained both pre- and intra-operatively along with the topographical scan of the eye are all stored in a memory of the laser surgery system. Software may be coded to automatically correlate the pre-operative retinal image to the topography, and also compare the pre- and intra-operative retinal images. The software may simply alert the surgeon as to any misalignment between the two retinal images, or may initiate an adjustment to the surgery system, such as rotation of a patient chair or control of the operating laser (e.g., such as during a keratotomy procedure).

Also, because of the pre-registration of the retinal image with the corneal topography, further measurements of the topography are not needed. Understanding of the retinal image once the patient is lying down can be translated into knowledge of the topography. Various laser eye surgery systems use different real-time imaging technology, typically OCT or Scheimpflug imaging. Precise control of the laser is informed by an understanding of the corneal topography, supplied by real-time retinal imaging. Preferably, the retina is imaged periodically during the procedure to adapt to any further patient movements.

A typical adjustment provided by the methods described herein is aligning the cuts made by the laser eye surgery system with a tilted steep axis of the cornea. The precise misalignment of the cornea as obtained by the retinal imaging in conjunction with topographical scanning guides a surgeon and proper placement of whatever therapeutic product or device is being applied to the eye. The guide could be a calculated measurement (i.e., degrees clockwise or counterclockwise misalignment) or can be incorporated to guide a surgeon to rotate the eye (or the head) a specific direction to gain proper alignment. Alternatively, the guide could be used to place a product or device (i.e., a toric intraocular lens) a specific amount for proper alignment.

One particular guide that may be useful is to place a reticle in the operating microscope to indicate toric intraocular lens alignment (or other therapeutic modalities) once the proper head position is verified with the system. The reticle can be a series of fine lines or fibers in the eyepiece of the microscope that indicates the steep axis of the cornea, or other characteristic misalignment. Insertion of toric intraocular lenses thus also may benefit from use of the present methodology, though the ultimate steps in the procedure do not involve a laser, but are rather manually accomplished.

Another application of the methodology disclosed herein is in registering and aligning laser therapy to the cornea, including Excimer ablations or laser-based arcuate keratotomies or other corneal incisions.

In general, the present eye registration methods are useful in a variety of ophthalmic procedures, with or without using a laser. Exemplary laser surgeries include cataract surgery, ablation of the cornea, or keratotomy, and the like. Laser systems including excimer lasers such as the Abbott Medical Optics' STAR S4 IR System, as well as femtosecond lasers such as the CATALYS Precision Laser System, and the intralase FS Laser may incorporate the techniques described herein. As mentioned above, insertion of a toric IOL will also be facilitated with knowledge of the steep meridian axis of the astigmatic eye provided by the retinal imaging and calibration, which does not involve a laser at all.

As mentioned above, a preferred method of retinal imaging is high-resolution videography or photography. However, other methods for retinal imaging are known, such as OCT, Zeiss scanners, and the like. High-resolution photography provides the greatest accuracy.

It should also be mentioned that the present application not only may provide a guide for rotational misalignment of the eye, such as with an astigmatic eye, but may also accommodate for translational movement during surgery. Consequently, the intraoperative adjustment may include a rotational and a translational component.

Finally, redundant observations may be made of secondary anatomical features of the eye to provide a check on the retinal imaging methods described above. For instance, iris and/or sclera landmarks may be noted in the pre-operative phase and referenced to the retinal image or topographical scan. Such secondary references may then be checked intra-operatively, along with the retinal image calibration, to ensure that they agree. If there is some discrepancy, the procedure may be halted and repeated. Of course, the preferred method is to use the retinal imaging which provides a highly detailed reference map of the eye with which to register the steep meridian axis of the astigmatic eye.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of eye surgery on an astigmatic patient, comprising:
    by a video camera of a laser eye surgery system, pre-operatively obtaining a first retinal image of a retinal vessel architecture or optic nerve of an eye of the patient;
    by an ocular coherence tomography (OCT) device of the laser eye surgery system, pre-operatively scanning a cornea of the eye to obtain a corneal topography scan of the eye;
    by a processor of the laser eye surgery system, correlating the first retinal image and the corneal topography scan to determine retinal landmarks associated with an astigmatic axis of the cornea of the eye;
    recording a location of the retinal landmarks in an optical system of the laser eye surgery system;
    by the video camera of the laser eye surgery system, obtaining a second retinal image of the retinal vessel architecture or optic nerve while the patient is positioned supine on a chair of the laser eye surgery system;
    by the processor of the laser eye surgery system, analyzing the second retinal image to gauge a misalignment of the eye compared to the first retinal image;
    adjusting the patient or the laser eye surgery system based on the misalignment and the correlation of the first retinal image and the corneal topography scan; and
    after the adjusting step, by the laser eye surgery system, performing an eye surgery in the cornea, a lens capsule, and/or a crystalline lens nucleus of the eye.

2. The method of claim 1, wherein the eye surgery is insertion of a toric intraocular lens, and the step of recording includes placing a reticle in the optical system.

3. The method of claim 1, wherein the eye surgery is insertion of a toric intraocular lens, and the step of adjusting the patient or the laser eye surgery system includes rotating the patient in the chair relative to the optical system.

4. The method of claim 3, wherein the step of adjusting the patient or the laser eye surgery system further includes translating the patient in the chair relative to the optical system.

5. The method of claim 1, wherein the eye surgery is cataract removal using the laser eye surgery system and intraocular lens replacement, and the step of recording comprises storing the retinal landmarks in a system memory of the laser eye surgery system.

6. The method of claim 1, wherein the eye surgery is keratotomy using the laser eye surgery system, and the step of recording comprises storing the retinal landmarks in a system memory of the laser eye surgery system.

7. The method of claim 6, wherein the step of adjusting the patient or the laser eye surgery system includes aligning cuts made by the laser eye surgery system with a tilted steep axis of the cornea.

8. The method of claim 1, wherein the step of performing the eye surgery on the eye is performed without scanning the cornea to obtain another corneal topography scan after the step of pre-operatively scanning the cornea to obtain the corneal topography scan.

9. A method of eye surgery on an astigmatic patient, comprising:
by a video camera of a laser eye surgery system, pre-operatively obtaining a first retinal image of a retinal vessel architecture or optic nerve of an eye of the patient;
by the laser eye surgery system, storing the first retinal image in a system memory of the laser eye surgery system having software;
by an ocular coherence tomography (OCT) device of the laser eye surgery system, pre-operatively scanning a cornea of the eye to obtain a corneal topography scan of the eye;
by a processor of the laser eye surgery system, correlating the first retinal image and the corneal topography scan to determine retinal landmarks associated with an astigmatic axis of the cornea of the eye and storing the correlation in the system memory;
by the video camera of the laser eye surgery system, obtaining a second retinal image of the retinal vessel architecture or optic nerve while the patient is positioned supine under the laser eye surgery system;
by the processor of the laser eye surgery system, analyzing the second retinal image to gauge a misalignment of the eye compared to the first retinal image stored in system memory;
by the processor of the laser eye surgery system, alerting the system software of any misalignment;
adjusting the patient or the laser eye surgery system based on the misalignment and correlation of the first and second retinal images and the corneal topography scan; and
after the adjusting step, by the laser eye surgery system, performing an eye surgery in the cornea, a lens capsule, and/or a crystalline lens nucleus of the eye.

10. The method of claim 9, wherein the wherein the eye surgery is insertion of a toric intraocular lens, and the step of recording includes placing a reticle in an optical system of the laser eye surgery system.

11. The method of claim 9, wherein the eye surgery is insertion of a toric intraocular lens, and the step of adjusting the patient or the laser eye surgery system includes rotating the patient in a chair configured for the eye surgery relative to an optical system of the laser eye surgery system.

12. The method of claim 11, wherein the step of adjusting the patient or the laser eye surgery system further includes translating the patient in the chair relative to the optical system.

13. The method of claim 9, wherein the eye surgery is cataract removal using the laser eye surgery system and intraocular lens replacement.

14. The method of claim 9, wherein the eye surgery is keratotomy using the laser eye surgery system.

15. The method of claim 14, wherein the step of adjusting the patient or the laser eye surgery system includes aligning cuts made by the laser eye surgery system with a tilted steep axis of the cornea.

16. The method of claim 9, wherein the step of performing the eye surgery on the eye is performed without scanning the cornea to obtain another corneal topography scan after the step of pre-operatively scanning the cornea to obtain the corneal topography scan.

* * * * *